(12) United States Patent
Bhide et al.

(10) Patent No.: US 11,491,144 B2
(45) Date of Patent: Nov. 8, 2022

(54) METHODS OF TREATING FRAGILE X MENTAL RETARDATION SYNDROME

(71) Applicants: The Florida State University Research Foundation, Incorporated, Tallahassee, FL (US); Avekshan LLC, Alachua, FL (US)

(72) Inventors: Pradeep G. Bhide, Tallahassee, FL (US); Deirdre McCarthy, Tallahassee, FL (US); Enrique Carrazana, Alachua, FL (US); John W. Cran, Alachua, FL (US)

(73) Assignees: The Florida State University Research Foundation, Incorporated, Tallahassee, FL (US); Avekshan LLC, Alachua, FL (US)

( * ) Notice: Subject to any disclaimer, the term of this patent is extended or adjusted under 35 U.S.C. 154(b) by 0 days.

(21) Appl. No.: 16/369,748

(22) Filed: Mar. 29, 2019

(65) Prior Publication Data
US 2019/0298703 A1    Oct. 3, 2019

Related U.S. Application Data

(60) Provisional application No. 62/650,818, filed on Mar. 30, 2018.

(51) Int. Cl.
*A61K 31/485* (2006.01)
*A61P 43/00* (2006.01)
*A61K 31/4375* (2006.01)

(52) U.S. Cl.
CPC .......... *A61K 31/4375* (2013.01); *A61P 43/00* (2018.01)

(58) Field of Classification Search
CPC ... A61K 31/485; A61K 31/4375; A61K 31/40
See application file for complete search history.

(56) References Cited

U.S. PATENT DOCUMENTS

| | | | |
|---|---|---|---|
| 9,623,023 B2 * | 4/2017 | Bhide | A61K 31/485 |
| 2007/0213644 A1 | 9/2007 | Pagel et al. | |
| 2009/0175819 A1 | 7/2009 | Priest et al. | |
| 2014/0113924 A1 * | 4/2014 | Bhide | A61K 31/485 |
| | | | 514/279 |
| 2015/0141274 A1 | 5/2015 | Friedman et al. | |

FOREIGN PATENT DOCUMENTS

| | | |
|---|---|---|
| EP | 0969015 A2 | 1/2000 |
| WO | WO-2011/020030 A2 | 2/2011 |
| WO | WO-2013/170000 A1 | 11/2013 |

OTHER PUBLICATIONS

Metcalf et al. Kappa opioid antagonists: past successes and future prospects, in Drug Addiction From Basic Research to Therapy, Rapaka R.S., Sadee W., Eds.; Springer New York, 2008, Chapter 25, pp. 395-431.*
Budimirovic et al. Dev. Neurosci. 2011,33, 379-394.*
Balcioglu et al., "Plasma and brain concentrations of oral therapeutic doses of methylphenidate and their impact on brain monoamine content in mice," available in PMC Dec. 1, 2010, published in final edited form as: Neuropharmacology. 57(7-8): 687-693 (2009) (15 pages).
Bergman et al., "Effects of cocaine and related drugs in nonhuman primates. III. Self-administration by squirrel monkeys," J Pharmacol Exp Ther. 251(1): 150-55 (1989).
Bhargava et al., "Kappa opioid receptor activity in spontaneously hypertensive rats," J Pharmacol Exp Ther. 245(2):460-465 (1988).
Biederman et al., "Does attention-deficit hyperactivity disorder impact the developmental course of drug and alcohol abuse and dependence?" Biol Psychiatry. 44(4):269-73 (1998).
Biederman et al., "Is ADHD a risk factor for psychoactive substance use disorders? Findings from a four-year prospective follow-up study," J Am Acad Child Adolesc Psychiatry. 36(1):21-29 (1997).
Biederman, "Attention-deficit/hyperactivity disorder: a selective overview," Biol Psychiatry. 57(11):1215-20 (2005).
Bolanos et al., "Effects of the kappa-opioid receptor agonist U-50,488 on morphine-induced place preference conditioning in the developing rat," Eur J Pharmacol. 317(1):1-8 (1996).
Bright, "Abuse of medications employed for the treatment of ADHD: results from a large-scale community survey," Medscape J Med. 10(5):111 (2008) (14 pages).
Broom et al., "Nonpeptidic delta-opioid receptor agonists reduce immobility in the forced swim assay in rats," Neuropsychopharmacology. 26(6):744-55 (2002).
Brown et al., "Treatment of attention-deficit/hyperactivity disorder: overview of the evidence," Pediatrics. 115(6):e749-57 (2005) (11 pages).
Bryant et al., "Pavlovian conditioning of multiple opioid-like responses in mice," Drug Alcohol Depend. 103(1-2):74-83 (2009).
Campbell et al., "Naltrexone in autistic children: behavioral symptoms and attentional learning," J Am Acad Child Adolesc Psychiatry. 32(6): 1283-91 (1993).
Carlezon et al., "Depressive-like effects of the kappa-opioid receptor agonist salvinorin A on behavior and neurochemistry in rats," J Pharmacol Exp Ther. 316(1):440-47 (2006).
Chefer et al., "Kappa-opioid receptor activiation prevents alterations in mesocortical dopamine neurotransmission that occur during abstinence from cocaine," Neuroscience. 101(3):619-27 (2000).
Cummings, "Frontal-subcortical circuits and human behavior," Arch Neurol. 50(8):873-80 (1993).
Dean et al., "Overriding the blockade of antinociceptive actions of opioids in rats treated with extended-release naltrexone," Pharmacol Biochem Behav. 89(4):515-22 (2008).
Di Chiara et al., "Drugs abused by humans preferentially increase synaptic dopamine concentrations in the mesolimbic system of freely moving rats," Proc Natl Acad Sci USA. 85(14): 5274-78 (1988).
Donahue et al., "Low-dose naltrexone targets the opioid growth factor-opioid growth factor receptor pathway to inhibit cell proliferation: mechanistic evidence from a tissue culture model," Exp Biol Med (Maywood). 236(9):1036-50 (2011) (16 pages).

(Continued)

*Primary Examiner* — Irina Neagu
(74) *Attorney, Agent, or Firm* — Clark & Elbing LLP

(57) ABSTRACT

The invention provides a method of treating FX syndrome and FX premutation by administering an effective amount of a κ-opioid receptor antagonist to an individual having FX syndrome or FX premutation.

11 Claims, 6 Drawing Sheets

(56) References Cited

OTHER PUBLICATIONS

Drake et al., "Kappa opioid receptor-like immunoreactivity in guinea pig brain: ultrastructural localization in presynaptic terminals in hippocampal formation," J Comp Neurol. 370(3):377-95 (1996).
Elchaar et al., "Efficacy and safety of naltrexone use in pediatric patients with autistic disorder," Ann Pharmacother. 40(6):1086-95 (2006).
Endoh et al., "Nor-binaltorphimine: a potent and selective kappa-opioid receptor antagonist with long-lasting activity in vivo," Arch Int Pharmacodyn Ther. 316:30-42 (1992) (Abstract only) (1 page).
Evans et al., "Cloning of a delta opioid receptor by functional expression," Science. 258(5090):1952-55 (1992).
Feldman et al., "Naltrexone and communication skills in young children with autism," J Am Acad Child Adolesc Psychiatry. 38(5):587-93 (1999).
Gerasimov et al., "[Treatment of patients with lumbar osteochondrosis by the method of intra-tissular electric stimulation]," Ortop Travmatol Protez. (5):13-17 (1991) (Abstract Only) (1 page).
Gossett et al., "Psychiatric disorders among women with the fragile X premutation without children affected by fragile X syndrome," Available in PMC Dec. 12, 2019, published in final edited form as: Am J Med Genet B Neuropsychiatr Genet. 171(8): 1139-47 (2016) (17 pages).
Hagerman et al., "Fagile X syndrome," Nat Rev Dis Primers. 3:17065 (2017) (19 pages).
Hauser et al., "Endogenous opioids regulate dendritic growth and spine formation in developing rat brain," Brain Res. 416(1):157-61 (1987).
Hellman et al., "Opioid microinjection into raphe magnus modulates cardiorespiratory function in mice and rats," Am J Physiol Regul Integr Comp Physiol. 297(5):R1400-8 (2009).
Huizink et al., "Maternal smoking, drinking or cannabis use during pregnancy and neurobehavioral and cognitive functioning in human offspring," Neurosci Biobehav Rev. 30(1):24-41 (2006).
Jomary et al., "Synaptic localization of kappa opioid receptors in guinea pig neostriatum," Proc Natl Acad Sci USA. 89(2): 564-68 (1992).
Jones et al., "Long term kappa-opioid receptor blockade following nor-binaltorphimine," Eur J Pharmacol. 215(2-3):345-48 (1992).
Kieffer et al., "The detla-opioid receptor: isolation of a cDNA by expression cloning and pharmacological characterization," Proc Natl Acad Sci USA. 89(24):12048-52 (1992).
Klein-Schwartz, "Abuse and toxicity of methylphenidate," Curr Opin Pediatr. 14(2):219-23 (2002).
Knoll et al., "Anxiolytic-like effects of kappa-opioid receptor antagonists in models of unlearned and learned fear in rats," J Pharmacol Exp Ther. 323(3):838-45 (2007).
Kuczenski et al., "Exposure of adolescent rats to oral methylphenidate: preferential effects on extracellular norepinephrine and absence of sensitization and cross-sensitization to methamphetamine," J Neurosci. 22(16): 7264-71 (2002).
Kuczenski et al., "Locomotor effects of acute and repeated threshold doses of amphetamine and methylphenidate: relative roles of dopamine and norepinephrine," J Pharmacol Exp Ther. 296(3): 876-83 (2001).
Kuczenski et al., "Stimulant actions in rodents: implications for attention-deficit/hyperactivity disorder treatment and potential substance abuse," Biol Psychiatry. 57(11):1391-96 (2005).
Li et al., "Molecular cloning and expression of a rat kappa opioid receptor," Biochem J. 295(Pt 3):629-33 (1993).
Linnet et al., "Maternal lifestyle factors in pregnancy risk of attention deficit hyperactivity disorder and associated behaviors: review of the current evidence," Am J Psychiatry. 160(60):1028-40 (2003).
Mahler et al., "What and when to "want"? Amygdala-based focusing of incentive salience upon sugar and sex," Psychopharmacology (Berl). 221(3):407-426 (2012).
Maisonneuve et al., "U50,488, a kappa opioid receptor agonist, attenuates cocaine-induced increases in extracellular dopamine in the nucleus accumbens of rats," Neurosci Lett. 181(1-2):57-60 (1994) (Abstract only) (1 page).
Margolis et al.,"Kappa opioids selectively control dopaminergic neurons projecting to the prefrontal cortex," Proc Natl Acad Sci USA. 103(8): 2938-42 (2006).
McLaughlin et al., "Diabetic keratopathy and treatment by modulation of the opioid growth factor (OGF)-OGF receptor (OGFr) axis with naltrexone: a review," Brain Res Bull. 81(2-3):236-47 (2010).
Meshul et al., "Kappa opioid receptor immunoreactivity in the nucleus accumbens and caudate-putamen is primarily associated with synaptic vesicles in axons," Neuroscience. 96(1):91-99 (2000).
Metcalf et al., "Kappa opioid antagonists: past successes and future prospects," The AAPS J. 7(3):E704-722 (2005).
Milberger et al., "Is maternal smoking during pregnancy a risk factor for attention deficit hyperactivity disorder in children?" Am J Psychiatry. 153(9):1138-42 (1996).
Mill, "Rodent models: Utility for candidate gene studies in human attention-deficit hyperactivity disorder (ADHD)," J Neursosci Methods. 166(2):294-305 (2007).
Olfson et al., "National trends in the use of psychotropic medications by children," J Am Acad Child Adolesc Psychiatry. 41(5):514-21 (2002).
Patkar et al., "Physical Presence of Nor-Binaltorphimine in Mouse Brain over 21 Days after a Single Administration Corresponds to Its Long-Lasting Antagonistic Effect on kappa-Opioid Receptors," J Pharmacol Exp Ther. 346(3):545-554 (2013).
Patrick et al., "Pharmacology of methylphenidate, amphetamine enantiomers and pemoline in attention-deficit hyperactivity disorder," Human Psychopharmacol. 12(6):527-46 (1997).
Pauly et al., "Maternal tobacco smoking, nicotine replacement and neurobehavioral development," Acta Paediatr. 97(10):1331-37 (2008).
Randall-Thompson et al., "A role for delta opioid receptors in the central nucleus of the amygdala in anxiety-like behaviors," Psychopharmacology (Berl). 212(4):585-95 (2010).
Recant et al. "Naltrexone reduces weight gain, alters "beta-endorphin", and reduces insulin output from pancreatic islets of genetically obese mice," Peptides. 1(4):309-13 (1980) (Abstract Only) (1 page).
Ren et al., "Prenatal L-DOPA exposure produces lasting changes in brain dopamine content, cocaine-induced dopamine release and cocaine conditioned place preference," Neuropharmacology. 60(2-30):295-302 (2011).
Robbins, "ADHD and addiction," Nat Med. 8(1):24-25 (2002).
Russell et al., Animal models of attention-deficit hyperactivity disorder, Behav Brain Funct. 1:9 (2005) (17 pages).
Sagvolden et al., "Rodent models of attention-deficit/hyperactivity disorder," Biol Psychiatry. 57(11):1239-47 (2005).
Sagvolden et al., "The spontaneously hypertensive rat model of ADHD—the importance of selecting the appropriate reference strain," Neuropharmacology. 57(7-8):619-626 (2009).
Schneider et al., "Prenatal exposure to nicotine impairs performance of the 5-choice serial reaction time task in adult rats," Neuropsychopharmacology. 36(5):1114-25 (2011).
Soderman et al., "Cocaine reward and hyperactivity in the rat: sites of mu opioid receptor modulation," Neuroscience. 154(4):1506-16 (2008).
Svingos et al., "Kappa-Opioid and NMDA glutamate receptors are differentially targeted within rat medial prefrontal cortex," Brain Res. 946(2):262-71 (2002).
Svingos et al., "Major coexpression of kappa-opioid receptors and the dopamine transporter in nucleus accumbens aconal profiles," Synapse. 42(3):185-92 (2001).
Svingos et al., "Mu-opioid receptors in the ventral tegmental area are targeted to presynaptically and directly modulate mesocortical projection neurons," Synapse. 41(3):221-29 (2001).
Takemori et al., "Nor-binaltorphimine, a highly selective kappa-opioid antagonist in analgesic and receptor binding assays," J Pharmacol Exp Ther. 246(1):255-58 (1988).
Thompson et al., "Kappa-opiod receptor activation modifies dopamine uptake in the nucleus accumbens and opposes the effects of cocaine," J Neurosci. 20(24): 9333-40 (2000).

(56) References Cited

OTHER PUBLICATIONS

Todtenkopf et al., "Effects of kappa-opioid receptor ligands on intracranial self-stimulation in rats," Psychopharmacology (Berl). 172(4):463-70 (2004).
Varaschin et al., "Selective mu- and kappa-opioid receptor antagonists administered into the nucleus accumbens interfere with rapid tolerance to ethanol in rats," Psychopharmacology (Berl). 206(1):85-96 (2009).
Volkow et al., "Comparable changes in synaptic dopamine induced by methylphenidate and by cocaine in the baboon brain," Synapse. 31(1):59-66 (1999).
Volkow et al., "Methylphenidate and cocaine have a similar in vivo potency to block dopamine transporters in the human brain," Life Sci. 65(1): PL7-12 (1999).
Volkow, "Stimulant medications: how to minimize their reinforcing effects?" Am J Psychiatry. 163(3): 359-61 (2006).
Wickstrom, "Effects of nicotine during pregnancy: human and experimental evidence," Curr Neuropharmacol. 5(3):213-22 (2007).
Wiley et al., "Kappa-opioid system regulates the long-lasting behavioral adaptations induced by early-life exposure to methylphenidate," Neuropsychopharmacology. 34(5):1339-50 (2009).
Willemsen-Swinkels et al., "The effects of chronic naltrexone treatment in young autisitc children: a double-blind placebo-controlled crossover study," Biol Psychiatry. 39(12):1023-31 (1996).
Yano et al., "Methylphenidate and cocaine: the same effects on gene regulation?" Trends Pharmacol Sci. 28(11):588-596 (2007).
You et al., "Modulation of neurotransmitter release in the basal ganglia of the rat brain by dynorphin peptides," J Pharmacol Exp Ther. 290(3):1307-15 (1999).
Zagon et al., "Endogenous opioid systems regulate cell proliferation in the developing rat brain," Brain Res. 412(1):68-72 (1987).
Zagon et al., "Increased brain size and cellular content in infant rats treated with an opiate antagonist," Science. 221(4616):1179-80 (1983).
Zagon et al., "Naltrexone modulates growth in infant rats," Life Sci. 33(24):2449-54 (1983).
Zagon, "Endogenous opioids, opioid receptors, and neuronal development," NIDA Res Monogr. 78:61-71 (1987).
Zhang et al., "Minocycline attenuates hyperlocomotion and prepulse inhibition deficits in mice after administration of the NMDA receptor antagonist dizocilpine," Neuropsychopharmacology. 32(9):2004-10 (2007).
Zhu et al., "Changes of releases of beta-endorphin-like immunoreactive substances and noradrenaline in rabbit's preoptic area during acupuncture analgesia," Sheng Li Xue Bao. 42(2):188-93 (1990) (Abstract Only) (1 page).
Zhu et al., "Cloning of a human kappa opioid receptor from the brain," Life Sci. 56(9):PL201-207 (1995).
Zhu et al., "Methylphenidate and mu opioid receptor interactions: a pharmacological target for prevention of stimulant abuse," available in PMC Jul. 1, 2012, published in final edited form as: Neuropharmacology. 61(1-2):283-92 (2011) (18 pages).
Zhu et al., "Prenatal nicotine exposure mouse model showing hyperactivity, reduced cingulate cortex volume, reduced dopamine turnover, and responsiveness to oral methylphenidate treatment," J Neurosci. 32(27): 9410-18 (2012).
Zhu et al., "The region in the mu opioid receptor conferring selectivity for sufentanil over the delta receptor is different from that over the kappa receptor," FEBS Lett. 384(2):198-202 (1996).
Zuvekas et al., "Recent trends in stimulant medication use among U.S. children," Am J Psychiatry. 163(4): 579-85 (2006).
Carreno-Munoz et al., "Potential involvement of impaired BKCa channel function in sensory defensiveness and some behavioral disturbances induced by unfamiliar environment in a mouse model of fragile X syndrome." Neuropsychopharmacology: Official Publication of the American College of Neuropsychopharmacology. 43(3): 492-502 (2018).
Crawley JN, "Designing mouse behavioral tasks relevant to autistic-like behaviors." Ment Retard Dev Disabil Res Rev. 10(4): 248-58 (2004).
Deacon RM, "Assessing nest building in mice." Nat Protoc. 1(3): 1117-9 (2006).
Gurney et al., "Multiple behavior phenotypes of the fragile-X syndrome mouse model respond to chronic inhibition of Phosphodiesterase-4D (PDE4D)." Sci Rep. 7(1): 14653 (2017) (11 pages).
Wadell et al., "Fragile X syndrome: psychiatric manifestations, assessment and emerging therapies." Curr Psychiatry Rev. 9(1): 53-58 (2013) (11 pages).
"Aticaprant," Wikipedia, <https://en.wikipedia.org/wiki/Aticaprant>, retrieved on Oct. 14, 2021 (5 pages).
Borghgraef et al., "Fragile (X) syndrome: a study of the psychological profile in 23 prepubertal patients," Clin Genet. 32(3): 179-86 (1987).
Lozano et al., "Fragile X spectrum disorders," Intractable Rare Dis Res. 3(4):134-46 (2014).
Tranfaglia, "The psychiatric presentation of Fragile X: evolution of the diagnosis and treatment of the psychiatric comorbidities of Fragile X syndrome," Dev Neurosci. 33(5):337-48 (2011).
Sullivan et al., "ADHD symptoms in children with FXS," Am J Med Genet A. 140(21): 2275-88 (2006).
Bailey et al., "Co-Occurring Conditions Associated with FMR1 Gene Variations: Findings from a National Parent Survey." Am J Med Genet A, 146A(16):2060-9 (2008).
Tranfaglia, "A Medication Guide for Fragile X," Version 5, 1-166 (2009).

* cited by examiner

METHODS OF TREATING FRAGILE X MENTAL RETARDATION SYNDROME

BACKGROUND OF THE INVENTION

Fragile X mental retardation syndrome (FX) is an inherited condition that causes a range of developmental disabilities, including delayed speech and language development, mild to moderate intellectual disability, anxiety, attention deficit, hyperactivity, communication and social deficits associated with autism spectrum disorder, and seizures (Hagerman et al. Nat. Rev. Dis. Primers 2017, 3, 17065). FX is a result of a mutation in the Fragile X mental retardation 1 (FMR1) gene. The mutation expands a DNA segment, known as the CGG triplet repeat, beyond its normal range of 5 to 40 repeats. An expansion in the 55-200 range constitutes a premutation, whereas an expansion beyond 200 repeats causes a full mutation or FX. The >200 range silences the FMR1 gene and interferes with the synthesis of the Fragile X mental retardation protein (FMRP), which is required for normal nervous system development and function (Hagerman et al. Nat. Rev. Dis. Primers 2017, 3, 17065). The premutation does not interfere with the production of FMRP but instead increases FMR1 messenger RNA expression. FX affects 1 in 4000 males and 1 in 6000 females of all races and ethnic groups. The prevalence of the premutation is significantly higher, affecting 1250 females and 1250-800 males. Women carrying the premutation have an increased risk for behavioral symptoms that overlap with the symptoms of FX, and include anxiety, depression, communication and social deficits, and obsessive-compulsiveness (Gossett et al. Am. J. Med. Genet. Part B 2016, 171B, 1139). FX is the number one inherited cause of intellectual disabilities, and the most common known cause of autism worldwide. Therefore, new methods for the treatment of premutation syndrome and FX are needed.

SUMMARY OF THE INVENTION

The invention provides a method of treating FX syndrome and FX premutation by administering an effective amount of a κ-opioid receptor antagonist to an individual having FX syndrome or FX premutation.

In some embodiments, the administering reduces the severity of a symptom. Exemplary symptoms are aggression, hyperactivity, impulsivity, social anxiety, attention deficit, repetitive behavior, seizures, impaired social interactions, motor impulsivity, and self-harm. In certain embodiments, the symptom is hyperactivity. In other embodiments, the symptom is social anxiety. In further embodiments, the symptom is aggression. In other embodiments the symptom is motor impulsivity, e.g., in females. In yet other embodiments, the symptom is repetitive behavior. In still further embodiments, the symptom is attention deficit. In other embodiments, the symptom is impaired social interactions.

In some embodiments, the κ-opioid receptor antagonist is a selective κ-opioid receptor antagonist. Exemplary selective κ-opioid receptor antagonists are norbinaltorphimine, PF4455242, (3R)-7-hydroxy-N-[(1S)-1-[[(3R,4R)-4-(3-hydroxyphenyl)-3,4-dimethyl-1-piperidinyl]methyl]-2-methylpropyl]-1,2,3,4-tetrahydro-3-isoquinolinecarboxamide, 3-((1R,3r,5S)-8-((5-methylthiophen-2-yl)methyl)-8-azabicyclo[3.2.1]octan-3-yloxy)benzamide, CERC-501, 5'-guanidinonaltrindole, 6'-guanidinonaltrindole, BU09059, hyperoside, 2-(3,4-dichlorophenyl)-N-methyl-N-[(1S)-1-(3-isothiocyanatophenyl)-2-(1-pyrrolidinyl)ethyl]acetamide hydrochloride, LY-2459989, LY-2795050, binaltorphimine, ML190, ML350, TENA, pawhuskin A, ethyl 4-(3-carbamoylbenzyl)-1-(cyclohexylmethyl)piperidine-4-carboxylate, and zyklophin. In certain embodiments, the κ-opioid receptor antagonist is norbinaltorphimine (nor-BNI).

In other embodiments, the κ-opioid receptor antagonist is a non-selective κ-opioid receptor antagonist. Exemplary non-selective κ-opioid receptor antagonist are LY-255582, alvimopan, naltrexone, apigenin, AT-076, axelopran, catechin, dezocine, 4',7-dihydroxyflavone, naloxone, nalmefene, amentoflavone, buprenorphine, methylnaltrexone, MR-2266, noribogaine, 6β-naltrexol-d4, 6β-naltrexol, and quadazocine.

In related embodiments, the κ-opioid receptor antagonist is administered for at least one week (e.g., two weeks, three weeks, four weeks, five weeks, six weeks, seven weeks, 8 weeks, 9 weeks, 10 weeks, 12 weeks, 15 weeks, 20 weeks, 30 weeks, 40 weeks, or 50 weeks).

In some embodiments, the κ-opioid receptor antagonist is administered at a dose of 0.1 to 50 mg/kg (e.g., 0.25-25 mg/kg). The dose may range from 0.5-5.0 mg/kg (e.g., 0.5, 1.0, 1.5, 2.0, 2.5, 3.0, 3.5, 4.0, 4.5, or 5.0 mg/kg) or from 5.0-20 mg/kg (e.g., 5.5, 6.0, 6.5, 7.0, 7.5, 8.0, 8.5, 9.0, 9.5, 10, 11, 12, 13, 14, 15, 16, 17, 18, 19, or 20 mg/kg).

In certain embodiments, the individual has FX syndrome. In other embodiments, the individual has FX premutation.

Definitions

The term "dose" refers to a single administration of an agent.

The term an "effective amount" of an agent, as used herein, is the amount sufficient to effect beneficial or desired results, such as clinical results, and an "effective amount" depends upon the context in which it is being applied. In the context of administering an agent that is a κ-opioid receptor antagonist, an effective amount of an agent is, for example, an amount sufficient to achieve a reduction in the severity of a symptom of Fragile X mental retardation syndrome as compared to the response obtained without administration of the agent.

The term "individual" refers to a mammal, e.g., a human.

The term "FX premutation" refers to a mutation in the FMR1 gene that consists of 55-200 CGG repeats.

The term "kappa (κ)-opioid receptor antagonist" refers to an agent (e.g., small molecule) that blocks or dampens a biological response of a κ-opioid receptor. A κ-opioid receptor antagonist may reduce receptor activity by directly binding to the receptor, by blocking the receptor binding site, by modulating receptor conformation (e.g., maintaining a receptor in a closed or inactive state), by preventing coupling between the receptor and its G-protein partner, or by activating intracellular signaling molecules or pathways that alter the length of receptor activation. A κ-opioid receptor antagonist may reduce receptor activity by 10%, 20%, 30%, 40%, 50%, 60%, 70%, 80%, 90%, 95%, 98% or more. A κ-opioid receptor antagonist may also completely block or inhibit receptor activity. Antagonist activity may be concentration-dependent or independent.

A "selective kappa (κ)-opioid receptor antagonist" is a κ-opioid receptor antagonist that preferentially acts on the κ-opioid receptor relative to other opioid receptors, e.g., delta or mu. In certain embodiments, the selective κ-opioid receptor antagonist has a $K_i$ for the kappa receptor at least two times lower relative to the delta and mu receptors, e.g., a $K_i$ at least 5, 10, 15, 20, 25, 30, 35, or 40 lower relative to the delta and mu receptor.

As used herein, the terms "treat," "treated," and "treating" mean therapeutic treatment, wherein the object is to prevent or slow down (lessen) an undesired physiological condition or obtain beneficial or desired clinical results. Beneficial or desired clinical results include, but are not limited to, alleviation of symptoms; diminishment of the extent of a condition; stabilized (i.e., not worsening) state of condition; delay in onset or slowing progression of condition; amelioration of the condition or remission (whether partial or total), whether detectable or undetectable; an amelioration of at least one measurable physical parameter, not necessarily discernible by the individual; or enhancement or improvement of condition. Treatment includes eliciting a clinically significant response without excessive levels of side effects.

DETAILED DESCRIPTION

Figure 1:
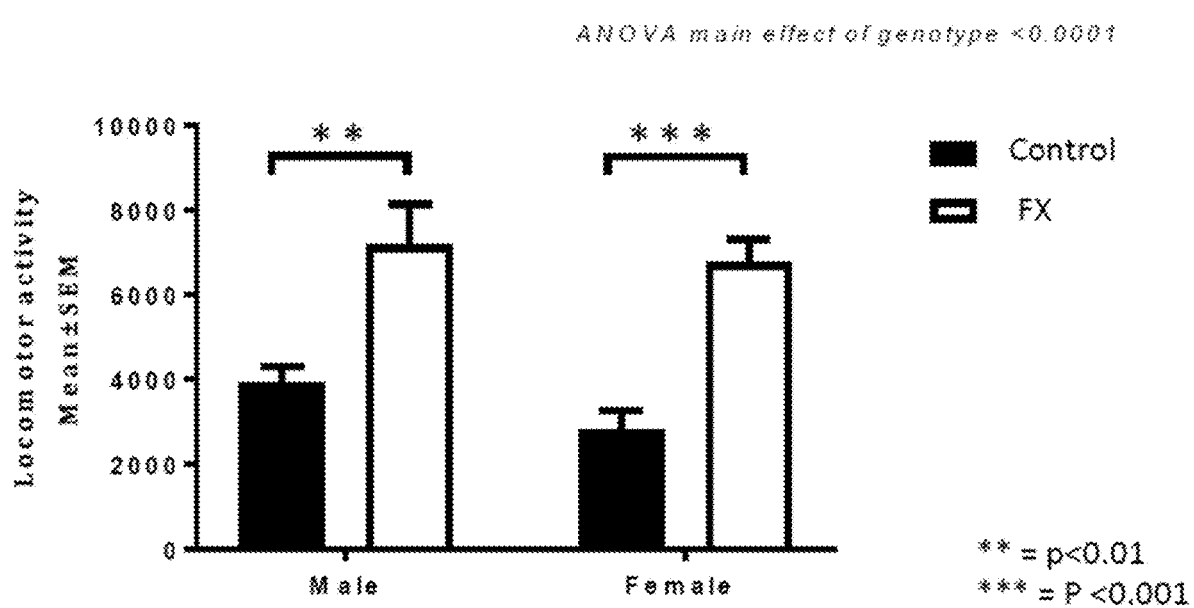
FIG. 1 is a graph showing spontaneous locomotor activity measured between 7 pm and 7 am, when the ambient lights are turned off. Nocturnal animals, such as mice, are naturally more active in the dark phase of the light-dark cycle, and locomotor activity during the dark phase represents their activity during their "waking" hours. Male and female Fragile X (FX) mice were more active than age-matched male and female control mice.

We have surprisingly discovered that administration of a κ-opioid receptor antagonist can be used to treat the behavioral symptoms associated with Fragile X mental retardation syndrome (FX) and the FX premutation. The administration may reduce the severity of a symptom including hyperactivity, aggression, impulsivity, social anxiety, attention deficit, repetitive behavior, seizures, impaired social interactions, motor impulsivity, and self-harm.

FX and FX premutation are genetic conditions involving changes in part of the X chromosome. These conditions cause a range of developmental problems, including learning disabilities and cognitive impairment. FX (full mutation or premutation) is the most common form of inherited intellectual disability in males and a significant cause of intellectual disability in females. Other signs and symptoms may include symptoms of autism spectrum disorders, seizures, and characteristic physical features. FX is caused by a mutation in the FMR1 gene and is inherited in an X-linked dominant manner. This gene carries instructions to make a protein called the fragile X mental retardation 1 protein. The FMR1 gene contains a section of DNA called a CGG triplet repeat, which normally repeats from 5 to around 40 times. In most cases of FX, this section of DNA is repeated more than 200 times, which "turns off" the FMR1 gene and disrupts the function of the nervous system. In a small portion of cases, other types of changes in the FMR1 gene cause FX. These changes may involve a deletion of all or part of the gene, or a change in the amino acids used to make the FMR protein. A premutation in the FMR1 gene consists of 55-200 CGG repeats. It does not "turn off" the FMR1 gene, nor does it reduce FMRP. Instead, the premutation increases FMR1 messenger RNA expression and is associated with behavioral symptoms that overlap with FX, e.g., anxiety, depression, communication and social deficits, and obsessive-compulsiveness.

κ-Opioid Receptor Antagonists

Suitable κ-opioid receptor antagonists are known in the art. In some embodiments, the κ-opioid receptor antagonist is a selective κ-opioid receptor antagonist. Exemplary selective κ-opioid receptor antagonists are norbinaltorphimine (nor-BNI), PF4455242, (3R)-7-hydroxy-N-[(1S)-1-[[(3R, 4R)-4-(3-hydroxyphenyl)-3,4-dimethyl-1-piperidinyl] methyl]-2-methylpropyl]-1,2,3,4-tetrahydro-3-isoquinolinecarboxamide (JDTic), 3-((1R,3r,5S)-8-((5-methylthiophen-2-yl)methyl)-8-azabicyclo[3.2.1]octan-3-yloxy)benzamide (AZ-MTAB), CERC-501 (LY2456302), 5'-guanidinonaltrindole (5'-GNTI), 6'-guanidinonaltrindole (6'-GNTI), BU09059, hyperoside, 2-(3,4-dichlorophenyl)-N-methyl-N-[(1S)-1-(3-isothiocyanatophenyl)-2-(1-pyrrolidinyl)ethyl] acetamide hydrochloride (DIPPA), LY-2459989, LY-2795050, binaltorphimine (BNI), ML190, ML350, TENA, pawhuskin A, zyklophin, and ethyl 4-(3-carbamoylbenzyl)-1-(cyclohexylmethyl)piperidine-4-carboxylate (AZ-ECPC). In some embodiments, the selective κ-opioid receptor antagonist is norbinaltorphimine (nor-BNI).

In alternative embodiments, the κ-opioid receptor antagonist is a non-selective κ-opioid receptor antagonist. Exemplary non-selective κ-opioid receptor antagonists are LY-255582, alvimopan, naltrexone, apigenin, AT-076, axelopran, catechin, dezocine, 4',7-dihydroxyflavone, naloxone, nalmefene, amentoflavone, buprenorphine, methylnaltrexone, MR-2266, noribogaine, 6β-naltrexol-d4, 6β-naltrexol, and quadazocine (WIN-44,441).

Pharmaceutical Compositions

A κ-opioid receptor antagonist is preferably formulated into pharmaceutical compositions for administration to individuals in a biologically compatible form suitable for administration in vivo. Accordingly, the present invention provides a pharmaceutical composition including a κ-opioid receptor antagonist in admixture with a suitable diluent, carrier, or excipient. The κ-opioid receptor antagonist can be formulated for extended, sustained, or immediate release to provide therapeutic amounts over a desired time period, e.g., a day, a week, two weeks, three weeks, or a month.

A κ-opioid receptor antagonist may be used in the form of the free base, in the form of a salt, solvate, or prodrug. All forms are within the scope of the invention. In accordance with the methods of the invention, the κ-opioid receptor antagonist may be administered to an individual in a variety of forms depending on the selected route of administration, as will be understood by those skilled in the art. A κ-opioid receptor antagonist may be administered, for example, by oral, parenteral, buccal, sublingual, nasal, rectal, patch, pump, or transdermal administration, and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A κ-opioid receptor antagonist may be administered orally, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the κ-opioid receptor antagonist may be incorporated with an excipient and used in the form of ingestible tablets, buccal tablets, troches, capsules, elixirs, suspensions, syrups, or wafers.

A κ-opioid receptor antagonist may also be administered parenterally. Solutions of the κ-opioid receptor antagonist can be prepared in water suitably mixed with a surfactant, such as hydroxypropylcellulose. Dispersions can also be prepared in glycerol, liquid polyethylene glycols, DMSO, and mixtures thereof, with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington: The Science and Practice of Pharmacy (2013, 22nd ed.) and in The United States Pharmacopeia: The National Formulary (USP 40 NF 35).

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer. Compositions suitable for buccal or sublingual administration include tablets, lozenges, and pastilles, where the active ingredient is formulated with a carrier, such as sugar, acacia, tragacanth, gelatin, and glycerin. Compositions for rectal administration are conveniently in the form of suppositories containing a conventional suppository base, such as cocoa butter.

A κ-opioid receptor antagonist may be administered to an individual, e.g., a human, alone or in combination with pharmaceutically acceptable carriers, as noted herein, the proportion of which is determined by the solubility and chemical nature of the κ-opioid receptor antagonist, chosen route of administration, and standard pharmaceutical practice.

Method of Treatment

A κ-opioid receptor antagonist may be administered to a patient with FX or FX premutation requiring treatment. The patient may be of any age, e.g., under two years of age, under 18 years of age, from 18 to 55 years of age, or over 55 years of age. Administration may occur one or more times during a day, e.g., 1, 2, 3, or 4 times a day. Administration may also occur during the day, e.g., morning and/or afternoon, to provide treatment during waking hours. Alternatively, administration may occur one or more times during a week or month, e.g., weekly, biweekly, or monthly administration. In some embodiments, the administration is lifelong. The reduction in symptoms of FX or FX premutation may be confirmed by patient, parent, caregiver, or healthcare professional (e.g., a nurse) reports or may be confirmed by more detailed patient-reported outcome scales and/or neuropsychological batteries.

The dosage of the κ-opioid receptor antagonist or a composition including the κ-opioid receptor antagonist, can vary depending on many factors, such as the pharmacodynamic properties of the κ-opioid receptor antagonist; the mode of administration; the age, health, and weight of the recipient; the nature and extent of the symptoms; the frequency of the treatment, and the type of concurrent treatment, if any; and the clearance rate of the κ-opioid receptor antagonist in the individual to be treated. One of skill in the art can determine the appropriate dosage. The κ-opioid receptor antagonist may be administered initially in a suitable dosage that may be adjusted as required, depending on the clinical response. In general, satisfactory results may be obtained when the κ-opioid receptor antagonist is administered to a human at a dosage of, for example, between 0.05 mg and 5000 mg (measured as the solid form). Dose ranges include, for example, between 1-4000 mg (e.g., 2000-4000, 1000-3000, 1-1000, 1-500, 1-100, or 5-80 mg).

Alternatively, the dosage amount can be calculated using the body weight of the individual. For example, the dose of a κ-opioid receptor antagonist, or pharmaceutical composition thereof, administered to an individual may range from 0.1-50 mg/kg (e.g., 0.25-25 mg/kg). In exemplary, non-limiting embodiments, the dose may range from 0.5-5.0 mg/kg (e.g., 0.5, 1.0, 1.5, 2.0, 2.5, 3.0, 3.5, 4.0, 4.5, or 5.0 mg/kg) or from 5.0-20 mg/kg (e.g., 5.5, 6.0, 6.5, 7.0, 7.5, 8.0, 8.5, 9.0, 9.5, 10, 11, 12, 13, 14, 15, 16, 17, 18, 19, or 20 mg/kg).

Examples

Methods

The B6.129P2-Fmr1$^{tm1Cgr}$/J strain of mouse was used in the studies as it is a widely used mouse model of FX (Kazdoba et al. Intractable Rare Dis. Res. 2014, 3, 118), and C57BL/6J mice were used as the control strain of mice. Mice were housed 2-4 per cage and maintained on a "reversed" light cycle (lights-off at 7 am and lights-on at 7 pm). They were habituated to the investigator by extensive handing for at least one week prior to the beginning of behavioral analyses. Additionally, they were habituated to the behavioral test room for at least 30 min prior to the behavioral testing, and testing was conducted under dim red light.

The mice underwent a battery of tests starting on postnatal day 60 (P60). Behavioral analyses included measurements of spontaneous locomotor activity, working memory, attention, and social interactions. Approximately 12 male and/or female mice were used for each behavioral test.

Spontaneous Locomotor Activity

Spontaneous locomotor activity was assayed by using a testing chamber with photobeam motion sensors (Photobeam Activity Systems, San Diego Instruments, San Diego, Calif.). During the testing period, mice were housed individually in the testing chamber for 16 h (12 h of which span the lights-off period when the rodents are most active). Photobeam breaks were recorded, scored as an ambulatory event, and grouped into hourly activity measurements for statistical analysis. Cumulative activity over the 12 hour "dark phase" was calculated. Changes (i.e., an increase or decrease) in locomotor activity in the FX mice are represented by changes (i.e., an increase or decrease) in the number of beam breaks compared to the beam breaks by the control groups of mice over a defined interval of analysis.

Working Memory

Working memory was assayed by using a mouse Y-maze. The maze had three arms of equal dimensions arranged in the shape of a Y. The order of arm entries was recorded and analyzed for spontaneous alternation (SA). Each arm was assigned a letter code (e.g., A, B, or C), and an alternation was scored for each set of three consecutive choices where no repeated entries occur. An alternation score ((# alternations/# of possible alternations)×100) was calculated. A mouse with working memory deficits has a lower alternation score compared to the baseline score in control groups.

Attention

Attention was assayed by using a mouse object-based attention test. The test apparatus consisted of a rectangular, two-chambered opaque Plexiglas box, including a training chamber where mice are exposed to five different objects, and smaller testing chamber where mice were exposed to two objects, one novel and one familiar. A recognition index was calculated as a ratio of time spent with the novel object to the total time with novel and familiar object. A mouse with attention deficit was expected not to favor the novel object, but focus equal attention on familiar and novel objects, and, hence, have a lower recognition index.

Impaired Social Interactions

In a test of social dominance (e.g., tube test, which evaluates aggression), the FX mice (both male and female) fail to display dominance. The lack of social dominance in this test is considered a measure of impaired social interactions.

Motor Impulsivity

Motor-impulsivity was assayed using a cliff avoidance reflex (CAR) test. The apparatus consists of a round Plexiglas platform (20 cm in diameter) supported by an iron rod (50 cm in height). The mouse is placed on the platform and observed over a period of 30 min. If the mouse falls off the platform during the 30 min period, it is picked up and returned to the platform to complete the test. The number of falls is recorded, and the data are analyzed at 5 min intervals.

Results

Figure 2:
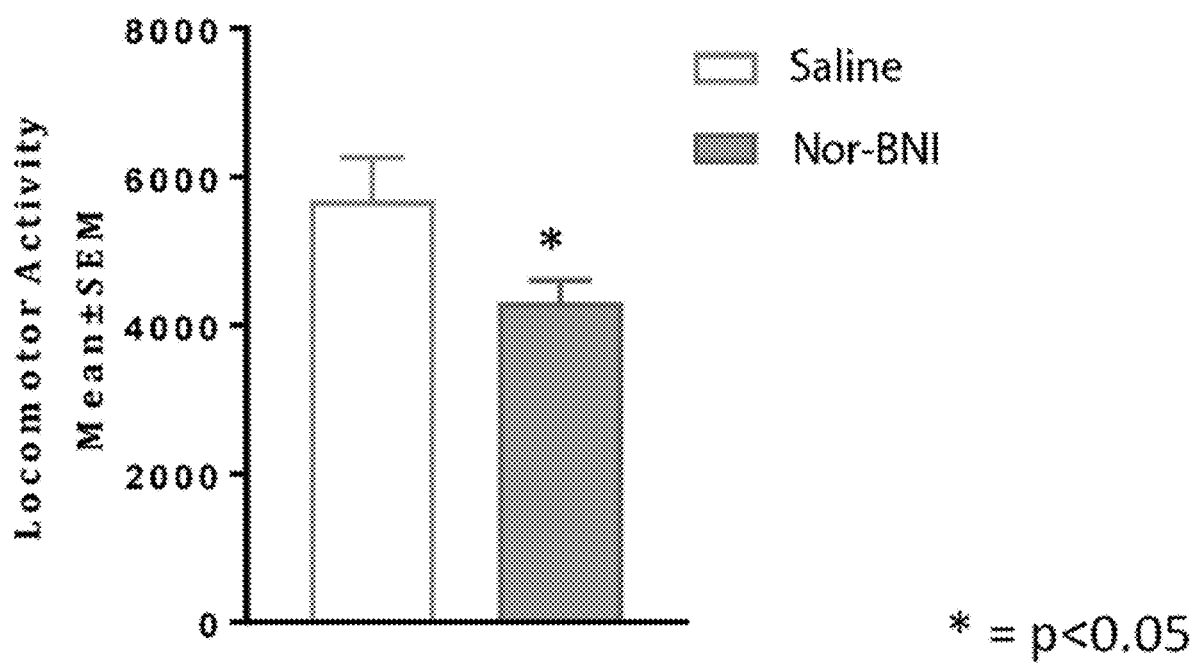
FIG. 2 is a graph showing spontaneous locomotor activity assays in which male FX mice were administered norbinaltorphimine (nor-BNI; 20 mg/kg; intraperitoneal) or saline (vehicle). Locomotor activity was measured between 7 pm and 7 am. Mice that received nor-BNI showed a significant reduction in activity compared to the mice that received saline.
Figure 3:
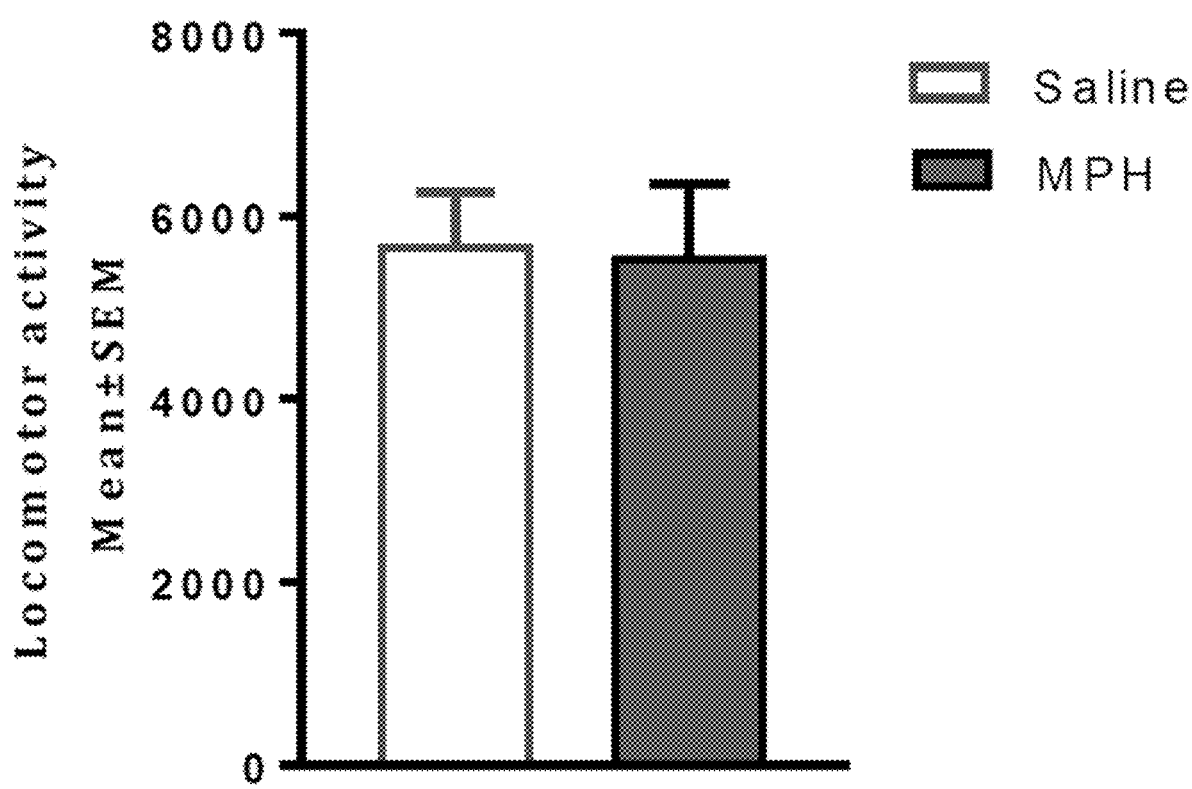
FIG. 3 is a graph showing spontaneous locomotor activity assays in which male FX mice were administered methylphenidate (MPH; 0.75 mg/kg; intraperitoneal) or saline (vehicle). Locomotor activity was measured between 7 pm and 7 am. Methylphenidate administration did not produce significant effects on the activity compared to saline administration.

Spontaneous locomotor activity was measured between 7 pm and 7 am, when the ambient lights were turned off. Nocturnal animals, such as mice, are naturally more active in the dark phase of the light-dark cycle, and locomotor activity during the dark phase represents their activity during "waking" hours. Both male and female FX mice were more active than the age-matched male and female control mice (FIG. 1). Spontaneous locomotor activity assays were performed in which male FX mice were administered nor-binaltorphimine (nor-BNI; 20 mg/kg; intraperitoneal) or saline (vehicle). Locomotor activity was measured between 7 pm and 7 am. Mice that received nor-BNI showed a reduction in activity compared to the mice that received saline (FIG. 2). Spontaneous locomotor activity assays were performed in which male FX male mice were administered methylphenidate (MPH; 0.75 mg/kg; intraperitoneal) or saline (vehicle). Locomotor activity was measured between 7 pm and 7 am. Methylphenidate administration did not produce significant effects on the activity compared to saline administration (FIG. 3).

Figure 4:
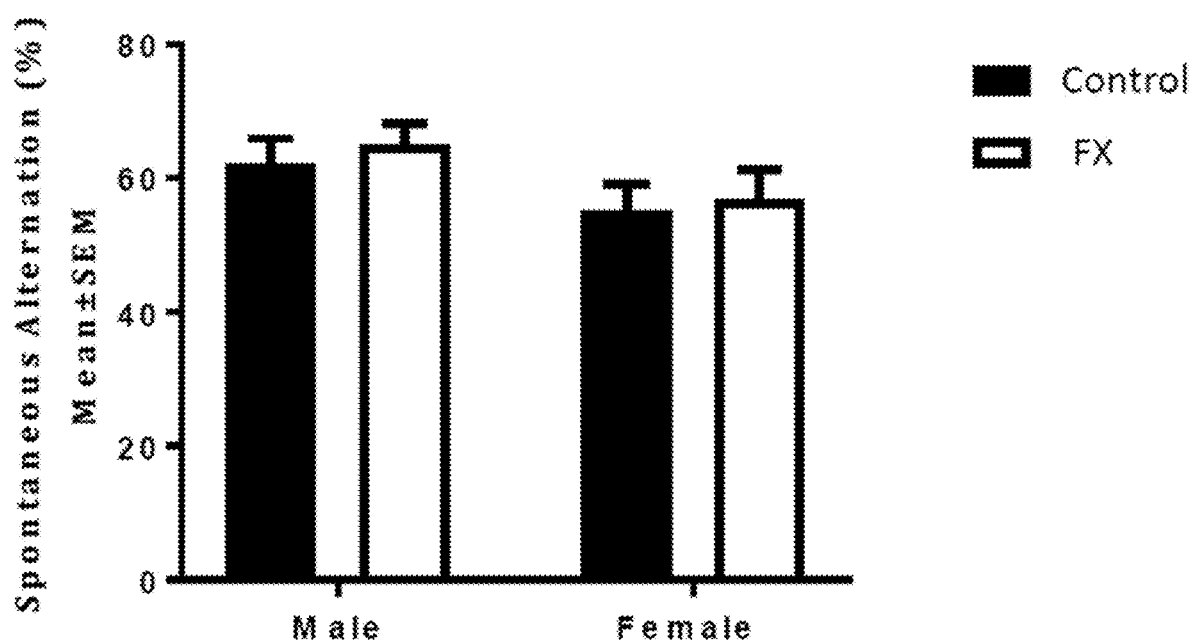
FIG. 4 is a graph showing a Y-maze (spatial working memory) assay. There was no significant difference in Y-maze performance between male or female FX mice and male and female control mice.
Figure 5:
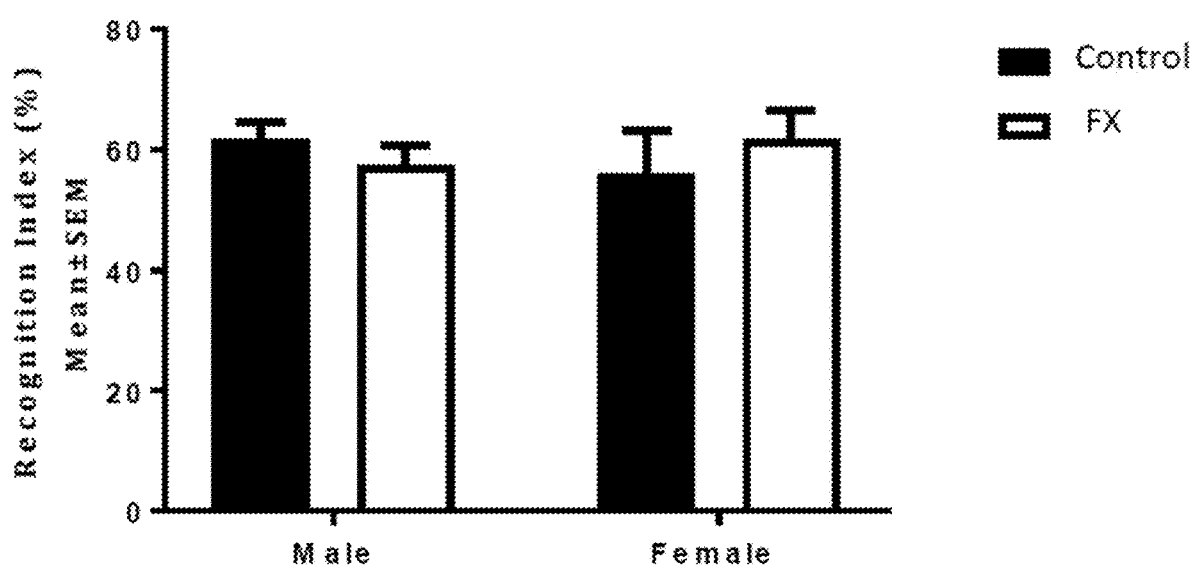
FIG. 5 is a graph showing an object-based attention assay. There was no significant difference in performance between male or female FX mice and male and female control mice.

Spontaneous alternation using a Y-maze assay to test spatial working memory was performed. There was no significant difference in Y-maze performance between male or female FX mice and male and female control mice (FIG. 4). An object-based attention assay was performed to measure recognition. There was no significant difference in performance between male or female FX mice and male and female control mice (FIG. 5).

Figure 6A:
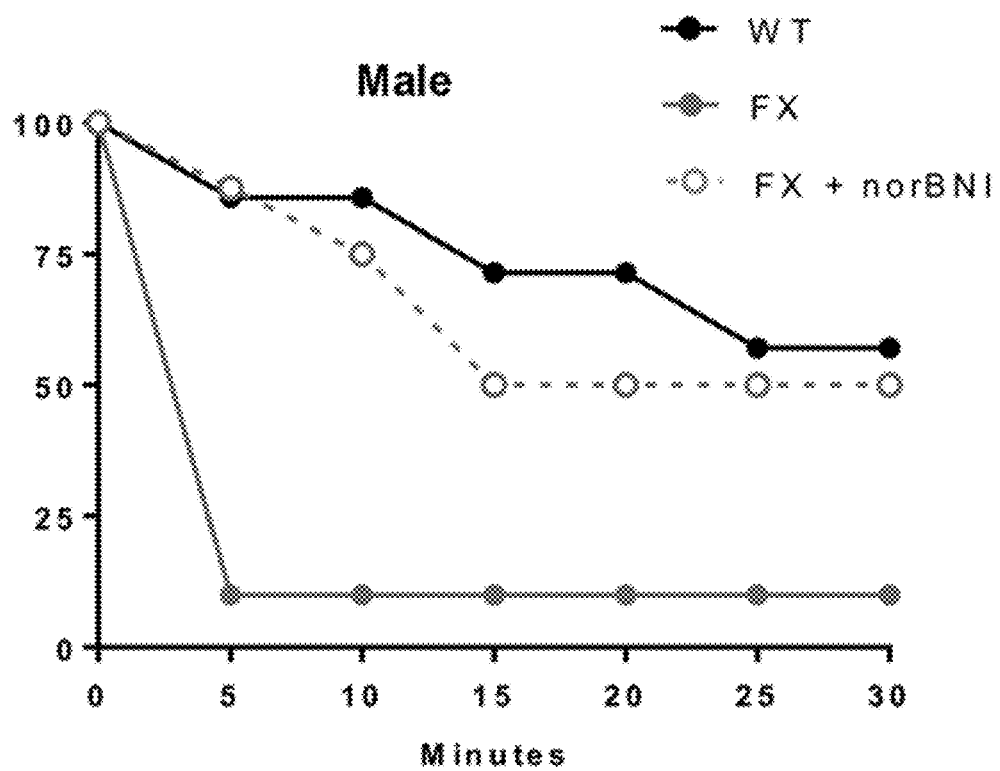
FIGS. 6A-6B are graphs showing the cliff avoidance reflex assay for motor impulsivity in which male and female FX mice were administered nor-binaltorphimine (nor-BNI; 20 mg/kg; intraperitoneal). Approximately 90% of the female FX mice and 50% of the male FX mice fell off the platform within the first 5 minutes of the test. Nor-binaltorphimine improved the time course of cliff avoidance reflex in the female FX mice (FIG. 6B) and did not produce significant effects in male FX mice (FIG. 6A).
Figure 6B:
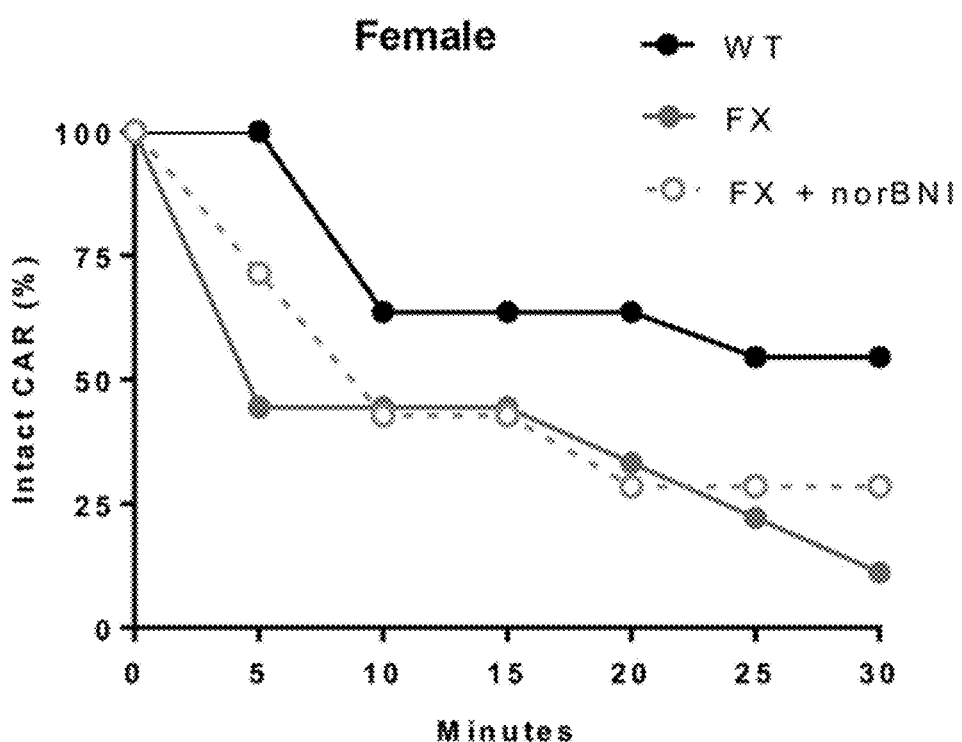

Male and female FX mice showed impaired cliff avoidance reflex. Approximately 90% of the female FX mice and 50% of the male FX mice fell off the platform within the first 5 minutes of the test (FIGS. 6A-6B). Nor-binaltorphimine (nor-BNI; 20 mg/kg; intraperitoneal) improved the time course of cliff avoidance reflex in the female FX mice (FIG. 6B) and did not produce significant effects in male FX mice (FIG. 6A).

Conclusion

Unlike in attention deficit hyperactivity disorder (ADHD) in which both methylphenidate and nor-BNI are effective, only nor-BNI was effective in alleviating hyperactivity in FX. Nor-BNI was also effective in ameliorating motor impulsivity. Nor-BNI produces long-lasting effects compared to other treatments for hyperactivity, such as stimulants (e.g., methylphenidate or amphetamine), and nor-BNI carries particular utility in the management of hyperactivity throughout the waking hours. Unlike stimulants, nor-BNI is not known to have abuse potential, and unlikely to be classified as a DEA schedule II controlled substance.

Other Embodiments

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

Where a term in the present application is found to be defined differently in a document incorporated herein by reference, the definition provided herein is to serve as the definition for the term.

Other embodiments are in the claims.

What is claimed is:

1. A method of treating Fragile X syndrome without attention-deficit hyperactivity disorder in an individual in need thereof, the method comprising administering an effective amount of a κ-opioid receptor antagonist to the individual, wherein the κ-opioid receptor antagonist is norbinaltorphimine or CERC-501.

2. The method of claim 1, wherein the administering reduces the severity of a symptom selected from the group consisting of aggression, impulsivity, social anxiety, repetitive behavior, seizures, impaired social interactions, motor impulsivity, and self-harm.

3. The method of claim 2, wherein the symptom is social anxiety.

4. The method of claim 2, wherein the symptom is aggression.

5. The method of claim 2, wherein the symptom is repetitive behavior.

6. The method of claim 2, wherein the symptom is impaired social interactions.

7. The method of claim 2, wherein the symptom is motor impulsivity.

8. The method of claim 1, wherein the κ-opioid receptor antagonist is CERC-501.

9. The method of claim 1, wherein the κ-opioid receptor antagonist is norbinaltorphimine.

10. The method of claim 1, wherein the κ-opioid receptor antagonist is administered for at least one week.

11. The method of claim 1, wherein the κ-opioid receptor antagonist is administered at a dose of 0.1 to 50 mg/kg.

* * * * *